United States Patent
Park et al.

(10) Patent No.: US 8,441,647 B2
(45) Date of Patent: May 14, 2013

(54) APPARATUS FOR DETECTING FOREIGN MATERIAL IN POUCH TYPE BATTERY

(75) Inventors: Seung Yeob Park, Daejeon (KR); Ho Sub Jung, Gwangmyeong-si (KR); Jin-Young Park, Daejeon (KR); Young Joon Shin, Daejeon (KR); Eun Ju Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 154 days.

(21) Appl. No.: 12/945,313

(22) Filed: Nov. 12, 2010

(65) Prior Publication Data

US 2011/0090507 A1    Apr. 21, 2011

Related U.S. Application Data

(63) Continuation-in-part of application No. PCT/KR2010/006256, filed on Sep. 14, 2010.

(30) Foreign Application Priority Data

Sep. 14, 2009 (KR) ........................ 10-2009-0086679

(51) Int. Cl.
*G01N 21/00* (2006.01)
*G01N 21/55* (2006.01)

(52) U.S. Cl.
USPC .................. 356/445; 356/237.1; 356/237.2

(58) Field of Classification Search ........... 356/445–448
See application file for complete search history.

(56) References Cited

U.S. PATENT DOCUMENTS

| | | | |
|---|---|---|---|
| 5,963,328 A | 10/1999 | Yoshida et al. | |
| 7,564,544 B2 * | 7/2009 | Zhao et al. | 356/237.2 |
| 2009/0000723 A1 * | 1/2009 | Engelbart et al. | 156/64 |

FOREIGN PATENT DOCUMENTS

| | | |
|---|---|---|
| JP | 6-265477 A | 9/1994 |
| JP | 2007-78404 A | 3/2007 |
| KR | 10-1999-024012 A | 3/1999 |
| KR | 10-2004-0020721 A | 3/2004 |

* cited by examiner

*Primary Examiner* — Michael P Stafira
(74) *Attorney, Agent, or Firm* — Birch, Stewart, Kolasch & Birch, LLP

(57) ABSTRACT

An apparatus and method for detecting a foreign material within a pouch type battery by performing a light scattering method on a surface of a battery case are provided. The apparatus for detecting a foreign material within a pouch type battery includes: a light source irradiating linear light to a surface of a battery case at a pre-set incident angle; a sensor unit sensing light reflected from the battery case; and a foreign material detection unit detecting the presence or absence of a foreign material and the position of the foreign material within a battery through the reflected light sensed by the sensing unit. A foreign material within a battery can to be quickly and accurately detected.

11 Claims, 1 Drawing Sheet

[FIG. 1]
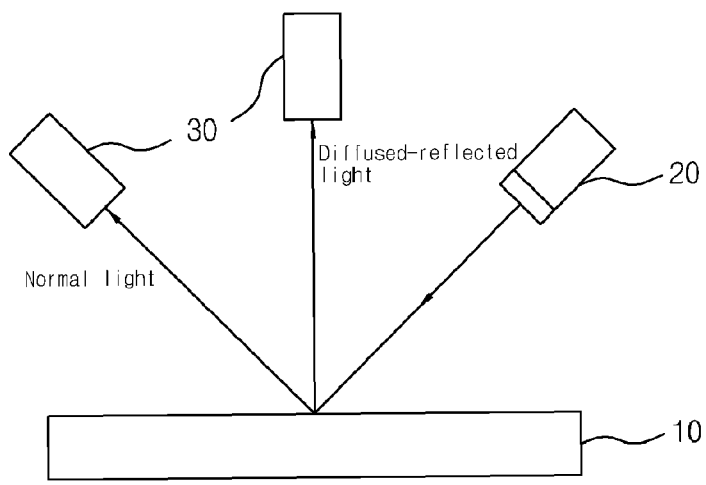
[FIG. 2]
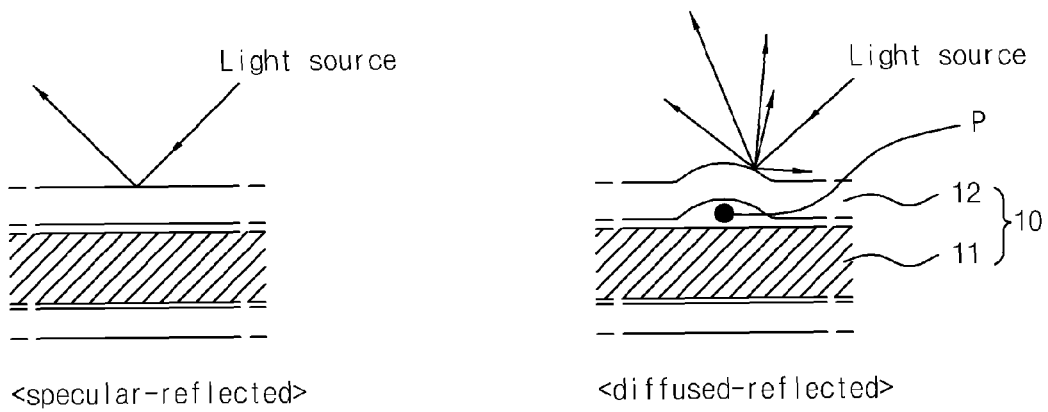
<specular-reflected>     <diffused-reflected>

APPARATUS FOR DETECTING FOREIGN MATERIAL IN POUCH TYPE BATTERY

The present application is a continuation-in-part application of International Application No. PCT/KR2010/006256, filed Sep. 14, 2010, which claims the benefit of Korean Patent Application No. 10-2009-0086679, filed Sep. 14, 2009. The disclosures of said applications are incorporated by reference herein.

BACKGROUND OF THE INVENTION

1. Field of the Invention

The present invention relates to an apparatus and method for detecting a foreign material within a pouch type battery and, more particularly, to an apparatus and method for discriminating whether or not there is a foreign material within a battery by using a light scattering method on a surface of a battery case.

2. Description of the Related Art

In general, a pouch type battery is manufactured such that an electrode assembly, in which a positive electrode, a separator, and a negative electrode are alternately stacked, is mounted between laminate sheets, and the laminated sheets are thermally compressed.

In the process of manufacturing the pouch type battery, the positive electrode or the negative electrode may be notched or punched according to a desired size as necessary in order to manufacture the electrode assembly. The positive electrode and the negative electrode may have a solid active material layer, and the solid active material layer contains components such as an active material, an inorganic filler, and the like, and in the course of notching or punching operation, such components of the solid active material layer may be exposed as dust or mote.

The exposed dust or mote may fall back on an undesired portion of the electrode assembly or may be mounted as a foreign material or debris between the laminate sheet and the electrode assembly. The thusly mounted dust foreign material causes an undesired reaction in a charging or discharging process of the battery, greatly impairing the stability of the battery.

Thus, inspection of checking as to whether or not there is a foreign material in the battery must be necessarily performed before a final product is supplied to the market, and in general, one of the simplest methods of inspecting the presence or absence of a foreign material in the pouch type battery is observing the surface of the pouch during the operation by a worker.

The pouch type battery is manufactured by laminating the electrode assembly and the laminate sheet by heat, so if there is a foreign material between the electrode assembly and the laminate sheet, the surface of the laminated sheet, namely, the surface of the battery case, would be protruded correspondingly according to the shape of the foreign material. Thus, based on this, a foreign material within the battery can be inspected by simply checking the surface of the battery case.

As mentioned above, the related art method for inspecting the surface of the battery case is performed by the worker's naked eyes.

However, the related art method has a problem in that, because the worker directly inspects the battery case, the inspection speed is low. In particular, recently, the pouch type battery production process is performed by automated equipment and the manufactured batteries are rapidly transported by a transfer conveyer, so it is not possible for the worker to inspect the batteries at the rate of the rapidly transferred batteries. Thus, a method of sampling the batteries for inspection is employed; however, recently, as the stability of batteries is greatly issued, a total inspection is frequently performed to inspect every battery. Thus, a device for quickly inspecting the surfaces of battery cases is urgently required.

In addition, because the related art method relies on the naked eye inspection, dust foreign material in a micro size cannot be detected. In most cases, dust generated in the process of manufacturing batteries is too small to be recognized by the naked eyes. Thus, a device for accurately inspecting the surfaces of battery cases is urgently required.

SUMMARY OF THE INVENTION

Thus, the inventor of the present application provides an apparatus and method for quickly and accurately discriminating whether or not there is a foreign material within a pouch type battery.

According to an aspect of the present invention, there is provided an apparatus for detecting a foreign material within a pouch type battery, including: a light source irradiating linear light to a surface of a battery case at a pre-set incident angle; a sensor unit sensing light reflected from the battery case; and a foreign material detection unit detecting the presence or absence of a foreign material and the position of the foreign material within a battery through the reflected light sensed by the sensing unit.

The pre-set incident angle may range from 20° to 70°.

The light source may be an LED laser.

The LED laser may be a line LED array.

The sensor unit may be a charge-coupled device (CCD) camera.

The CD camera may be a line CCD camera.

According to another aspect of the present invention, there is provided a method for detecting a foreign material within a pouch type battery, including: irradiating linear light to a surface of a battery case at a pre-set incident angle; sensing, by a sensor, light reflected from the battery case; and when the incident angle of the linear light and the reflection angle of the reflected light are not identical, or when the linear light is diffused-reflected, determining that there is a foreign material within the pouch type battery.

The pre-set incident angle may range from 20° to 70°.

In determining whether or not the incident angle of the linear light and the reflection angle of the reflected light are not identical, when the sensor is set at a position of the reflection angle such that the reflection angle is identical to the pre-set incident angle and if the light source does not reach the set position, it may be determined that the incident angle of the linear light and the reflection angle of the reflected light are not identical.

In determining whether or not the incident angle of the linear light and the reflection angle of the reflected light are not identical, when the sensor is set at a position of the reflection angle different from the pre-set incident angle and if the light source reaches the set position, it may be determined that the incident angle of the linear light and the reflection angle of the reflected light are not identical.

In determining whether or not the linear light is diffused-reflected, the sensor is set at a position of the reflection angle different from the incident angle and if the light source reaches the set position, it may be determined that the incident angle of the linear light and the reflection angle of the reflected light are not identical.

According to another aspect of the present invention, there is provided a pouch type battery which undergoes a foreign material detection process by the foreign material detection apparatus or the foreign material detection method.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic view showing an example of a detection apparatus according to an exemplary embodiment of the present invention; and FIG. 2 is a schematic view showing the principle of diffused-reflection of linear light when there is a foreign material within a battery.

DETAILED DESCRIPTION OF THE INVENTION

An apparatus and method for detecting a foreign material within a pouch type battery according to exemplary embodiments of the present invention will now be described with reference to the accompanying drawings.

The present invention relates to an apparatus for detecting a foreign material within a pouch type battery, including: a light source irradiating linear light to a surface of a battery case at a pre-set incident angle; a sensor unit sensing light reflected from the battery case; and a foreign material detection unit detecting the presence or absence of a foreign material and the position of the foreign material within a battery through the reflected light sensed by the sensing unit.

According to an exemplary embodiment of the present invention, the presence or absence of a foreign material is detected by using a so-called 'light scattering method'. In the related art, the surface of semiconductor silicon wafer has been inspected by using an illumination device such as a laser, a halogen lamp, an infrared LED, or the like, and an optical device using a detection sensor such as a PMT (PhotoMultiply Tube), CCD (Charge Coupled Device), or the like, but those illumination device and the optical device have not been used for measuring a surface of a battery case.

FIG. 2 schematically illustrates the characteristics of the present invention of detecting the presence or absence of a foreign material by using the so-called 'light scattering method'.

FIG. 1 shows an example of the detection apparatus according to an exemplary embodiment of the present invention.

In an exemplary embodiment of the present invention, preferably, it is desirable that the incident angle of the light source ranges from 20° to 70°, in particular, within 30° to 60°. This is because an effective diffuse-reflection takes place within the incident angle range. Namely, when there is a foreign material (P) within a battery 10 including an electrode assembly 11 and a battery case 12, a protrusion from the battery case 12 is formed, and in this case, the protrusion has a convex parabola shape as shown in FIG. 2, so diffused-reflection can take place from the protrusion within the foregoing angle range.

In an exemplary embodiment of the present invention, as the light source 20, an LED laser may be used. In particular, preferably, the LED layer is a line LED array. This is because, if a pointy laser is used, the entirety of the surface of the battery cannot be quickly scanned. Namely, the line type laser is fixedly used, and when the battery transferred by a transfer conveyer passes through the fixed light source, the surface of the battery case can be quickly and entirely measured.

Preferably, the LED laser includes various types of wavelengths, rather than a single wavelength. If only a particular wavelength is confined, a foreign material may be detected or may not be detected according to the wavelength range.

In an exemplary embodiment of the present invention, the sensor unit 30 may be configured by using various light source detection sensors without any limitation, and in particular, preferably, a CCD camera is used as the sensor unit. The CCD camera may digitally converts a collected image, so it can easily store a data image, and the size, shape, and the height of an uneven portion of the surface of the battery case can be checked by analyzing the data image.

In particular, the CCD camera is a line CCD camera. As discussed above, because the line type light source is preferred, rather than a pointy light source, so in the same point of view, the line type camera is preferred as the sensor unit 30.

Two or more sensor units may be provided, and preferably, in order to improve the accuracy of detection of a foreign material, a plurality of sensor units may be positioned at various angles.

In an exemplary embodiment of the present invention, the foreign material detection unit (not shown) determines whether or not there is a foreign material upon receiving a signal detected by the sensor unit 30. When an incident angle of the linear light and a reflection angle of the reflected light are not identical or when the linear light is diffused-reflected, the foreign material detection unit determines that there is a foreign material within the pouch type battery. Namely, when the sensor is set at a position of the reflection angle such that it is the same as the pre-set incident angle, if the light source does not reach the position, or when the sensor is installed at a position of the reflection angle different from the incident angle, if the light source reaches the position, the foreign material detection unit may determine that there is a foreign material.

Any device can be used as the foreign material detection unit without any limitation, so long as it can receive a signal detected by the sensor unit and process it. Such a device may be, for example, a personal computer, a microcomputer, firmware, and the like.

Also, the present invention relates to a method for detecting a foreign material within a pouch type battery, including: irradiating linear light to a surface of a battery case at a pre-set incident angle; sensing, by a sensor, light reflected from the battery case; and when the incident angle of the linear light and the reflection angle of the reflected light are not identical, or when the linear light is diffused-reflected, determining that there is a foreign material within the pouch type battery.

In an exemplary embodiment of the present invention, preferably, the pre-set incident angle ranges from 20° to 70°, and the reason is as described above.

In an exemplary embodiment of the present invention, the sensor may be configured by using various light source detection sensors without any limitation, and in particular, preferably, a CCD camera is used as the sensor unit.

In determining whether or not the incident angle of the linear light and the reflection angle of the reflected light are not identical, when the sensor is set at a position of the reflection angle such that the reflection angle is identical to the pre-set incident angle and if the light source does not reach the set position, it may be determined that the incident angle of the linear light and the reflection angle of the reflected light are not identical. Also, when the sensor is set at a position of the reflection angle different from the pre-set incident angle and if the light source reaches the set position, it may be determined that the incident angle of the linear light and the reflection angle of the reflected light are not identical.

In an exemplary embodiment of the present invention, in determining whether or not the linear light is diffused-reflected, the sensor is set at a position of the reflection angle different from the incident angle and if the light source reaches the set position, it may be determined that the incident angle of the linear light and the reflection angle of the reflected light are not identical. In order to accurately detect whether or not the linear light is diffused-reflected, preferably, a plurality of CCD cameras are set at various angles.

As the present invention may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An apparatus for detecting a foreign material within a pouch type battery, the apparatus comprising:
   a light source irradiating linear light to a surface of a battery case at a pre-set incident angle;
   a sensor unit sensing light reflected from the battery case; and
   a foreign material detection unit detecting a presence or absence of the foreign material and a position of the foreign material within the pouch type battery through the reflected light sensed by the sensing unit,
   wherein the sensor unit is set at a position of a reflection angle such that the reflection angle is identical to the pre-set incident angle.

2. The apparatus of claim 1, wherein the pre-set incident angle ranges from 20° to 70°.

3. The apparatus of claim 1, wherein the light source is a light emitting diode (LED) laser.

4. The apparatus of claim 3, wherein the LED laser is a line LED array.

5. The apparatus of claim 1, wherein the sensor unit is a charge-coupled device (CCD) camera.

6. The apparatus of claim 5, wherein the CD camera is a line CCD camera.

7. A method for detecting a foreign material within a pouch type battery, the method comprising:
   irradiating linear light to a surface of a battery case at a pre-set incident angle;
   sensing, by a sensor, light reflected from the battery case; and
   when the pre-set incident angle of the linear light and a reflection angle of the reflected light are not identical, or when the linear light is diffused-reflected, determining that there is the foreign material within the pouch type battery.

8. The method of claim 7, wherein the pre-set incident angle ranges from 20° to 70°.

9. The method of claim 7, wherein, in determining whether or not the pre-set incident angle of the linear light and the reflection angle of the reflected light are not identical, when the sensor is set at a position of the reflection angle such that the reflection angle is identical to the pre-set incident angle and if a light source does not reach the set position, it is determined that the pre-set incident angle of the linear light and the reflection angle of the reflected light are not identical.

10. A pouch type battery which undergoes a foreign material detection process by the foreign material detection apparatus of claim 1.

11. A pouch type battery which undergoes a foreign material detection process by the foreign material detection method of claim 7.

* * * * *